(12) United States Patent
Bruins

(10) Patent No.: US 8,184,274 B2
(45) Date of Patent: May 22, 2012

(54) MEASURING INSTRUMENT AND METHOD FOR THE MEASURING OF PROPERTIES OF A PARTICULATE SAMPLE

(76) Inventor: Hans Joachim Bruins, Munich (DE)

(*) Notice: Subject to any disclaimer, the term of this patent is extended or adjusted under 35 U.S.C. 154(b) by 309 days.

(21) Appl. No.: 12/503,348

(22) Filed: Jul. 15, 2009

(65) Prior Publication Data

US 2010/0014070 A1    Jan. 21, 2010

(30) Foreign Application Priority Data

Jul. 21, 2008   (DE) .......................... 10 2008 033 979

(51) Int. Cl.
*G01N 21/00* (2006.01)
(52) U.S. Cl. ........................................................ 356/72
(58) Field of Classification Search ........................ None
See application file for complete search history.

(56) References Cited

U.S. PATENT DOCUMENTS

| 5,487,702 | A  | * | 1/1996  | Campbell et al. ................. 73/73 |
| 5,733,592 | A  |   | 3/1998  | Wettstein et al. |
| 6,646,264 | B1 | * | 11/2003 | Modiano et al. ............. 356/326 |
| 6,706,989 | B2 |   | 3/2004  | Hunter et al. |
| 7,508,501 | B2 | * | 3/2009  | Zubkov et al. .................. 356/73 |

FOREIGN PATENT DOCUMENTS

| DE | 4339285 A1 | 6/1994 |
| DE | 10119763 A1 | 10/2002 |
| DE | 10332800 B3 | 5/2005 |
| DE | 102005052769 A1 | 5/2007 |
| WO | 9958959 A1 | 11/1999 |
| WO | 02086473 A2 | 10/2002 |
| WO | 2005010505 A1 | 2/2005 |

* cited by examiner

*Primary Examiner* — Kara E Geisel
(74) *Attorney, Agent, or Firm* — Caesar, Rivise, Bernstein, Cohen & Pokotilow, Ltd.

(57) ABSTRACT

A measuring instrument (100) for measuring the properties of a sample (10) with a multitude of particles (11), including a spectroscopy device (20) to measure spectroscopic properties of the sample, and a weighing device (30) to measure the mass of the sample. Also described is a method for measuring the properties of a sample (10) with a multitude of particles (11).

15 Claims, 2 Drawing Sheets

MEASURING INSTRUMENT AND METHOD FOR THE MEASURING OF PROPERTIES OF A PARTICULATE SAMPLE

BACKGROUND

The invention concerns a measuring instrument for the measuring of properties of a sample which comprises a multitude of particles, such as for example of a plant sample, in particular a cereal sample, wherein the measuring instrument is equipped with a spectroscopy device, with which the spectroscopic properties of the sample can be measured. The invention further concerns a method for measuring properties of a sample which comprises a multitude of particles, wherein a measuring of spectroscopic properties of the sample with a spectroscopy device is provided. Applications of the invention are given in the characterization of particulate samples, in particular in the characterization of plant samples, e.g. of cereal samples.

It is well known to characterize the physical and chemical state of grain through the measuring of spectroscopic properties of the grain. For example, by a spectroscopic measurement the protein content of the grain can be ascertained. The spectroscopic measuring is typically not carried out on individual cereal grain, but on a sample with a multitude of cereal grain. Measuring instruments which are designed for the spectroscopic measuring of grain are for example described in DE 101 197 63 A1 and in DE 103 32 800 A1.

The use of the conventional measuring instruments is limited to the spectroscopic measurement. In practice this may prove disadvantageous, as often further properties, such as for example the specific weight of the cereal grain, have to be ascertained which cannot be derived directly from the spectroscopic properties. Thus further measurements are necessary for which a sample must be transferred from the spectroscopic measuring instrument to another measuring device or, if appropriate, provided in another state of preparation (e.g. larger sample quantities).

The measuring of the specific weight of cereals is for example necessary for the establishment of an insect attack or for an accurate characterization of the moisture contents. With an insect attack the sample contains hollow cereal grain, which is not identifiable with the spectroscopic measuring. For example healthy wheat has a specific weight of 80 kg/hl. A fall below this level may indicate an insect attack.

Hitherto it has been usual in practice to measure the specific weight of grain in that a grain sample is weighed in a measuring tube with a predetermined volume. This method has several disadvantages. Firstly a considerably greater sample volume is needed than this is necessary for spectroscopic measurement. The results are an increased material consumption and a limited comparability of the measurements of the spectroscopic properties and the specific weight. Secondly the conventional method means a high expenditure of time. The slow measurement requiring a careful filling of the grain into the measuring tube is impractical under the conditions of grain technology, for example after the harvest or on a depot. Finally, the conventional technology has a limited reproducibility. The relative weight can only be ascertained with an accuracy of about 10%, which is insufficient for a quantification of a possibly existing insect attack.

There are also measuring instruments known (e.g. U.S. Pat. No. 6,706,989 B2, DE 10 2005 052 769 A1 and DE 43 39 285 A1) for a spectroscopic measurement and a weight measurement for seed, which, however, do not allow a mass density determination on seed.

The disadvantages of conventional measurements on grain mentioned are also given in the measuring of other samples in the form of particles, such as other plant samples or plastic granulates in the plastics industry. For example, it may be necessary for quality monitoring in addition to the chemical composition of plastic particles to ascertain with spectroscopic measurements also physical parameters, such as for example the specific weight.

The objective of the invention is to provide an improved measuring instrument for the characterization of a particulate sample to avoid the disadvantages of the conventional technologies. The measuring instrument must in particular make possible that in addition to the spectroscopic measurement further measurements can be ascertained on the sample with increased accuracy and reproducibility. The objective of the invention is also to provide an improved measuring method to overcome the limitations of the conventional technologies and having a broadened range of application. A further objective of the invention is to indicate applications of the measuring instrument and of the measuring method.

These objectives are solved by a measuring instrument, a grain transporting device and a method of the invention.

SUMMARY OF THE INVENTION

In relation to the device the objective of the invention is solved by the general technical teaching to provide a generic measuring instrument for the measuring of properties of a sample with a multitude of particles, including a spectroscopy device for the measurement of spectroscopic properties of the sample, with a weighing device to measure the mass of the sample. Preferably, the spectroscopy device and the weighing device are integrated into a common measuring instrument. The spectroscopy device and the weighing device are connected with each other in the measuring instrument. A sample introduced into the measuring instrument can be subjected to spectroscopic measurement and weight measurement with the measuring instrument.

In relation to the method the objective of the invention is solved by the general technical teaching to measure properties of a sample with a multitude of particles with the sample being both subjected to a spectroscopic measurement and weighed. The spectroscopic measuring and the weighing (measurement of the mass) can take place on an identical sample. Successive measurements of the spectroscopic properties and the mass or a simultaneous measurement of both values can be provided.

The invention uses advantageously that a sample for spectroscopic measurement is arranged in a sample chamber through which the light path of the spectroscopy device runs. The sample chamber has a predetermined volume, which cannot be changed for measuring the sample. By connecting the spectroscopy device and the weighing device, the weighing of the sample filling the sample chamber of the spectroscopy device can be carried out. The measured mass and the known volume of the sample chamber allow to directly calculating the specific weight of the sample in accordance with the invention. Thereby the measuring of spectroscopic properties and of the specific weight can be considerably accelerated. Measurement errors due to the use of different sample parts or the use of the conventional meter tube technology are avoided. The inventor has found out that the specific weight of grain can be ascertained with a considerably higher accuracy of up to +/−0.2 kg/hl.

The term "spectroscopic properties" designates at least one parameter of the sample, which characterizes the interaction of the sample with light, in particular with at least one wavelength in a spectral region, extending from the UV wavelength over the visible area to the IR wavelengths. Preferably, the spectroscopy device is set up for measuring of the transmission, the optical density and/or the reflection of the sample at one or more wavelengths.

Advantageously, different variants exist to combine the spectroscopy device and the weighing device. For example the weighing device can be directly connected with the sample chamber of the spectroscopy device. In this case the spectroscopic properties and the mass of the sample can be measured at the same time. However, embodiments of the invention are preferred, in which the spectroscopy device and the weighing device are arranged adjacent to each other, for example one above the other or next to each other with the sample being completely transferable between the spectroscopy device and the weighing device. It can for example be provided that first the spectroscopic properties and subsequently the mass of the sample are measured. Alternatively, in reverse to this the measurement of the spectroscopic properties can be provided after weighing the sample.

Preferably the measuring instrument according to the invention is equipped with a transport wheel to transport the sample into the light path of the spectroscopy device. Advantageously, the transport wheel can transport the sample from the spectroscopy device to a sample holder of the weighing device. Particularly preferred is a variant of the invention, wherein at least one chamber of the transport wheel is used as a sample chamber for the spectroscopy device, as for example described in DE 103 32 800 A1. The transport wheel fulfils a triple function. Firstly, the transport wheel serves for the transport of the sample into the spectroscopy device. Secondly, the transport wheel provides the sample chamber for the spectroscopic measurement and a predetermined volume for the weighing. Thirdly, the transport wheel serves to transport the sample from the spectroscopy device to the sample holder of the weighing device. Finally, the transport wheel can also be provided for a densification movement which is described in DE 103 32 800 A1.

Preferably, the weighing device is arranged such that the sample under the effect of gravity can be moved from the spectroscopy device, in particular from the transport wheel, to the sample holder of the weighing device. The sample moves by free fall or gliding along an inclined path from the spectroscopy device to the weighing device. Advantageously, thus the measuring can be accelerated and it is ensured that the whole sample is subjected both to the spectroscopic measurement and to the weighing.

Advantageously, different types of weighing devices can be used. For example the weighing device may comprise a beam balance. In this case, advantages can rise for the integration of the weighing device into the housing of the measuring instrument. Furthermore the weighing device may comprise a spring balance, which may have advantages for the operation and cleaning of the weighing device. A combination of a beam balance and a spring balance may also be provided.

According to a further preferred embodiment of the invention the measuring instrument is equipped with an evaluation device with which the mass density (or: the specific weight) of the sample can be determined. The evaluation device is connected with the weighing device in order to calculate the mass density of the sample from a measurement signal of the weighing device, which is characteristic for the mass of the weighed sample, and the volume of the sample chamber in the spectroscopy device.

The measuring according to the invention is generally usable on samples of particle-shaped natural products, in particular agricultural products in the form of seed or fruit bodies, such as for example grain, maize, soy, rice, or samples made of synthetic particles, in particular plastic particles or granulates. Typical particle sizes are in the range of 0.1 to 20 mm, in particular from 1 mm to 10 mm, particularly preferred from 2 mm to 8 mm. The invention is particularly preferred when used in measurement of agricultural products. For this purpose the measuring instrument according to the invention is preferably part of a transport device for the agricultural product, for example of a grain transporting device. The measuring instrument according to the invention can for example be provided on a harvesting machine, such as for example a combined harvester or a transport machine, such as for example in a grain depot.

According to a further variant of the invention the sample can comprise several partial samples, which are subject to spectroscopic measurement and weighing. The partial samples can for example be separately measured spectroscopically and weighed. Alternatively, the partial samples can be spectroscopically measured separately and weighed jointly. Particularly preferred is an embodiment of the invention with the transport wheel for the transport of the sample in the measuring instrument comprising several transport chambers which are each provided for receiving one partial sample. The partial samples are each transported into the light path of the spectroscopy device and transported from this to the sample holder of the weighing device. Preferably, the weighing of the sample comprises the transfer of a multitude of grain samples from several filled transport chambers to the sample holder and the determination of the total weight of the partial samples.

BRIEF DESCRIPTION OF SEVERAL VIEWS OF THE DRAWINGS

Further details and advantages of the invention are described below in relation to the enclosed drawings, which show in.

DETAILED DESCRIPTION OF PREFERRED EMBODIMENTS

Embodiments of the invention are explained below with reference by way of example to the measurement of grain, in particular with the instrument described in DE 103 32 800 A1. It is emphasized that the implementation of the invention in practice is not limited to the equipment of the conventional instrument with the weighing device, but it is correspondingly possible with other measuring instruments. The invention is described below with reference to the combination of the spectroscopy device with the weighing device. Details of the spectroscopic measurement, in particular of the transport of the sample into the spectroscopy device, of the structure of the spectroscopy device and of the evaluation of the spectroscopic measurement are known per se to the person skilled in the art from the conventional spectroscopy technology and in particular the patent applications DE 101 197 63 A1 and DE 103 32 800 A1 and are hence not described here.

The application of the invention is not limited to the measurement of grain, but correspondingly possible on other plant products or on synthetic particles. Finally, it is to be noted that the embodiments of the invention are described with reference for example to a table instrument for use for example in a laboratory. Alternatively, the combination of a spectroscopy device with a weighing device can be provided on machines of grain technology which are in particular operated mobile or stationary.

Figure 1:
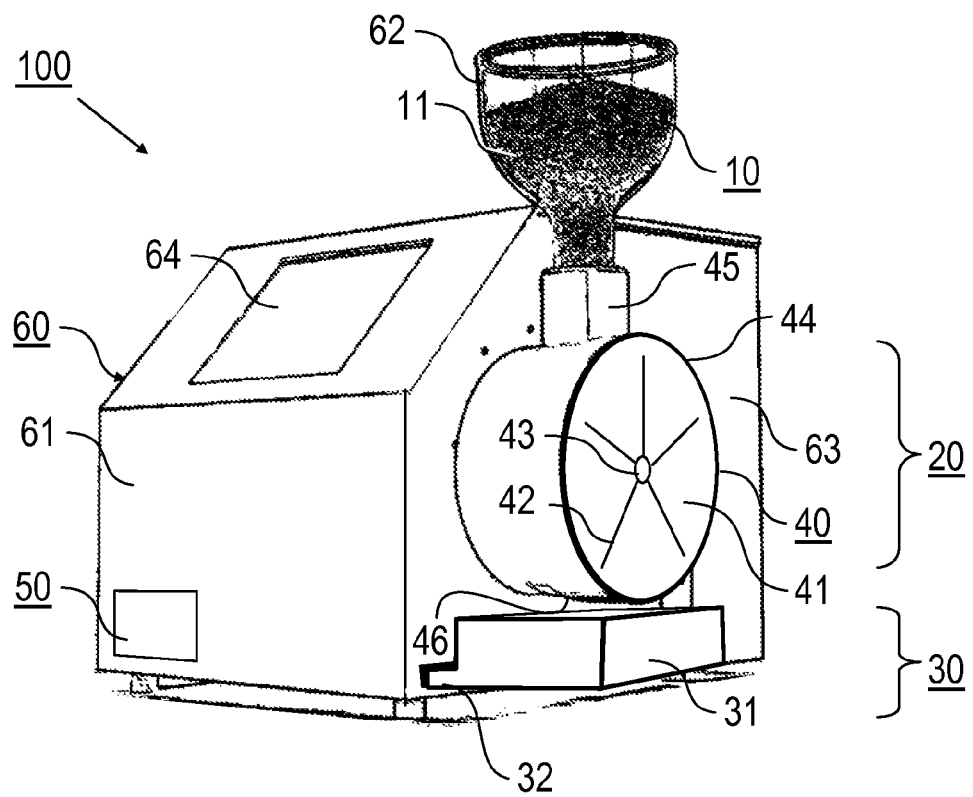
FIG. 1: a schematic illustration of an embodiment of the measuring instrument according to the invention.

FIG. 1 shows a preferred embodiment of the measuring instrument 100 according to the invention for the measurement of properties of a sample 10 with a multitude of particles 11 with a spectroscopy device 20, a weighing device 30, a transport wheel 40 and an evaluation device 50. The components 20 to 50 are arranged on and/or in a housing 60 of the measuring instrument 100.

The spectroscopy device 20 comprises an illumination device and a detector device (not shown), between which a light path runs through a sample chamber. The sample chamber is formed by one respective transport chamber 41 of the transport wheel 40 (bucket wheel). Advantageously, the spectroscopic measurement of the sample (or partial sample) can take place in the transport chamber 41. Details of the composition from the spectroscopy device 20 and the transport wheel 40 are described in DE 103 32 800 A1.

The transport wheel 40 comprises five vanes 42, between which the transport chambers 41 are formed each with a volume $V_{TK}$, in a transport wheel housing 44. The vanes 42 are level plates which project radially from, a central carrier 43 at equal angle intervals. The vanes 42 (schematically shown) and the illumination or detector unit of the spectroscopy device 20 are arranged in the transport wheel housing 44. The transport wheel housing 44 has an upper opening through which the sample 10 falls from a funnel 62 into the transport chamber 41 correspondingly situated under the upper opening 45. On actuation of the transport wheel 40 the transport chamber 41 in each case filled with the sample is moved into the light path of the detector device 20, where the spectroscopic measurement occurs. Thereby the next transport chamber 41 is filled at the upper opening 45 of the transport wheel housing. At the next step-wise actuations of the transport wheel 40, after the spectroscopic measurement the sample is moved to the lower opening 46 of the transport wheel housing 44, through which the sample falls or slides to the sample holder 31 of the weighing device 30.

Figure 2:
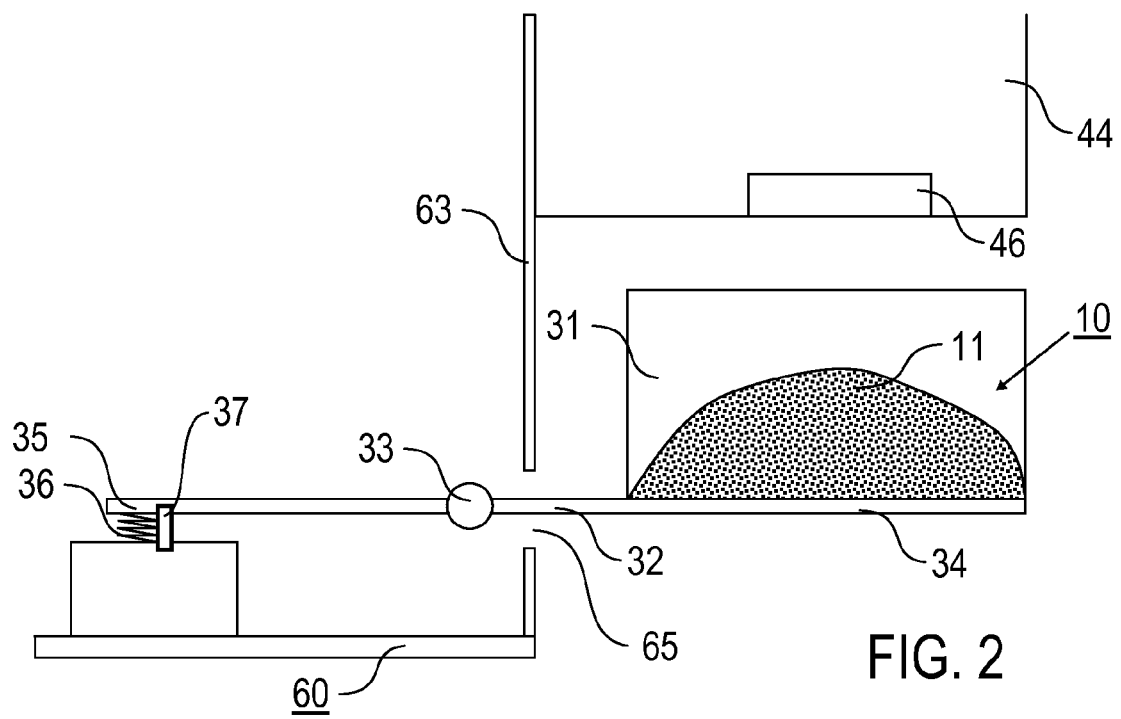
FIGS. 2 and 3: schematic sectional views of different variants of balances used according to the invention.
Figure 3:
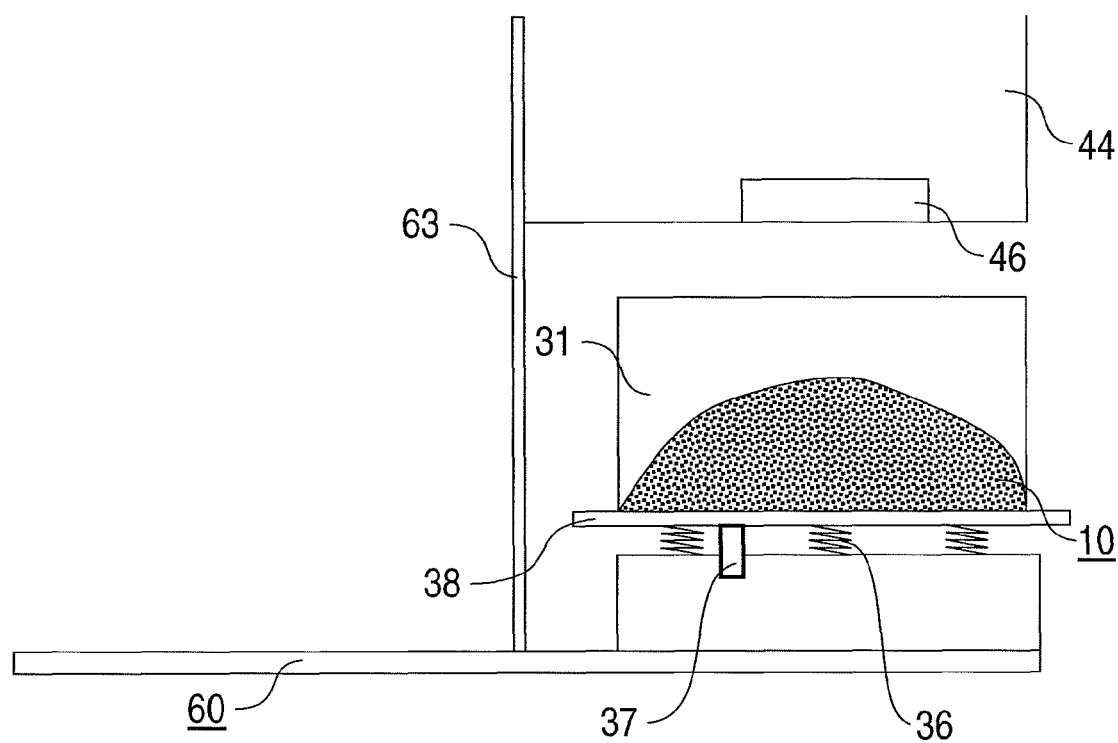

The weighing device 30 comprises for example a beam balance (FIGS. 1, 2) or a spring balance (FIG. 3). The production of the invention is in practice not limited to these types of scales, but is possible with other known scales per se for the determination of the mass of the goods being weighed. Details of the weighing device 30 are described with reference to FIGS. 2 and 3.

The housing 60 comprises several housing walls. In a front housing wall 61 a window is arranged for a display device 64. The display device 64 may comprise a touch-sensitive screen (Touch-Screen), to operate the measuring instrument 100. The transport wheel housing 44 is connected with a side wall 63. Beneath the transport wheel housing 44 the side wall 63 has an opening 65 for protruding of a lever arm 32 of the weighing device 30 (see FIG. 2).

FIG. 1 shows for illustrative purposes schematically on the front side wall 61 the evaluation device 50. In practice the evaluation device 50 can be provided at any suitable place in or outside the housing 60. The evaluation device 50 can for example be part of a computer circuit to also control the spectroscopy device 20 and the weighing device 30. The measuring signals of the spectroscopy device 20 and the weighing device 30 can alternatively be entered via an interface to an external evaluation device, such as for example an external computer.

The determination according to the invention of the mass density (specific weight) of a grain sample is carried out according to a first variant in such a way that the sample is filled into a transport chamber 41 of the transport wheel 40 and moved into the light path of the spectroscopy device 20. After the spectroscopic measurement the sample is dispatched to the sample holder 31 of the weighing device 30 in order to measure the mass of the sample. The known volume $V_{TK}$ of the transport chamber 41 and the measured mass m result in the specific weight according to $\rho=m/V_{TK}$. According to a second variant several partial samples in several transport chambers 41 are successively measured spectroscopically and successively moved to the sample holder 31. The measured total mass M there results in the specific weight in this case according to $\rho=M/(n \cdot V_{TK})$. Preferably the number n of the partial samples measured in each case in a separate transport chamber 41 is selected equal to the total number of the transport chambers 41 of the transport wheel 40. Thus with advantage potential errors through volume differences of the individual transport chambers can be avoided.

The accuracy of the mass density determined can still be improved in that the measuring is repeated on partial samples. For example the measuring with a transport wheel 40 with five transport chambers 41 (i.e. with five part measurements per sample) can be repeated with five samples, so that in the spectroscopic measurement altogether 25 measurement values are taken into consideration. Depending on the required accuracy of measurement the number of the part measurements can be even more increased.

The weighing device 30 may comprise a beam balance, which is illustrated in schematic cross section in FIG. 2. The weighing device in this case comprises a weighing arm 32, which is arranged pivotably around an axis of rotation 33 and whose free end 34 carries a sample holder 31, while the opposite end 35 is connected with the housing 60 via an flexibly deformable force element 36, such as for example a spring element. The axis of rotation 33 may be arranged inside (as shown) or outside the housing 60. The lever arm 32 projects through the opening 35 of the side wall 63 of the housing in such a way that the sample holder 31 is arranged below the lower opening 46 of the transport wheel housing 44. The force element 36 is equipped with a sensor 37, such as a strain gauge, in order to determine at the loading of the sample holder 31 with the sample 10 the pivoting of the lever arm. From the signal of the sensor 37 the weight of the sample 10 can be determined with the evaluation device 50 (FIG. 1).

According to FIG. 3 the weighing device 30 comprises a spring balance, with which the sample holder 31 is arranged on a platform 38 which is connected via force elements, for example spiral springs 36 with the stationary bottom plate of the housing 60. With a sensor 37 for example a strain gauge, the displacement of the platform 38 at the loading of the sample holder 31 with the sample 10 can be determined.

Deviating from the embodiments of the invention shown, the weighing device 30 can be formed such that the sample holder 31 and the remaining parts of the weighing device are arranged inside the housing 60. In this case, advantages may rise an improved safeguarding of the weighing device against contaminations or mechanical damage. For transfer of the sample from the transport wheel 40 to the sample holder 31, a chute is provided in this case forming a path from the lower opening 46 of the transport wheel housing 44 to the sample holder 31 of the weighing device 30 inside the housing 60.

The invention is not limited to the above described preferred examples of embodiment. Rather, there is a multitude of variants and derivations possible which also make use of the invention's concepts and therefore fall within the area of protection.

What is claimed is:

1. A measuring instrument for measuring properties of a sample with a multitude of particles, comprising:
   a spectroscopy device for measuring spectroscopic properties of the sample, wherein a sample chamber is provided, in which the sample can be arranged in the spectroscopy device and which has a predetermined volume, which cannot be changed for measuring the sample, and
   a weighing device for measuring a mass of the sample, wherein
   the spectroscopy device and the weighing device are arranged such that the sample is completely transferable from the sample chamber to the weighing device, such that the mass of the sample can be measured, which fills the sample chamber of the spectroscopy device, and
   an evaluation device is provided to determine a mass density of the sample from the measured mass and the volume of the sample chamber.

2. The measuring instrument according to claim 1, wherein a transport wheel is provided, to transport the sample into a light path of the spectroscopy device and from the spectroscopy device to a sample holder of the weighing device.

3. The measuring instrument according to claim 2, wherein the weighing device is arranged such that the sample can be moved under an influence of gravity from the transport wheel to the sample holder.

4. The measuring instrument according to claim 3, wherein:
   the transport wheel has several transport chambers, and
   the weighing device is configured for weighing of the sample in such a way that successive partial samples are transferred from all filled transport chambers to the sample holder.

5. The measuring instrument according to claim 1, wherein the weighing device comprises at least one of a lever and a spring balance.

6. The measuring instrument according to claim 1, wherein the spectroscopy device is set up for measuring at least one of a transmission, an optical density and a reflection of the sample.

7. The measuring instrument according to claim 1, which is part of a grain transporting device.

8. A method for measurement of properties of a sample with a multitude of particles using the measuring instrument of claim 1, comprising the steps:
   measuring of spectroscopic properties of the sample with the spectroscopy device,
   weighing the sample with the weighing device to determine a mass of the sample, and
   determining with the evaluation device the mass density of the sample from the mass and the volume of the sample chamber wherein
   the sample is completely transferred from the sample chamber of the spectroscopy device to the weighing device.

9. The method according to claim 8, wherein the sample is transported with a transport wheel into a light path of the spectroscopy device and from the spectroscopy device to a sample holder of the weighing device.

10. The method according to claim 8, wherein the transport wheel comprises several transport chambers and the weighing of the sample with the weighing device comprises a transfer of at least one partial sample from at least one of the transport chambers to the sample holder.

11. The method according to claim 10, wherein the weighing of the sample with the weighing device comprises a transfer of partial samples from all filled transport chambers to the sample holder.

12. The method according to claim 9, wherein the sample is moved under an influence of gravity from the transport wheel to the sample holder.

13. The method according to claim 8, wherein the measuring of the spectroscopic properties of the sample comprises a measurement of at least one of a transmission of the optical density and of a reflection of the sample.

14. The method according to claim 8, wherein the sample comprises particle-shaped agricultural products or synthetic particles.

15. The method according to claim 14, wherein the products are grains.

* * * * *